United States Patent
Morishima

(10) Patent No.: US 10,859,067 B2
(45) Date of Patent: Dec. 8, 2020

(54) VARIABLE STIFFNESS ACTUATOR

(71) Applicant: OLYMPUS CORPORATION, Tokyo (JP)

(72) Inventor: Tetsuya Morishima, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/375,936

(22) Filed: Apr. 5, 2019

(65) Prior Publication Data

US 2019/0234386 A1    Aug. 1, 2019

Related U.S. Application Data

(63) Continuation of application No. PCT/JP2016/082632, filed on Nov. 2, 2016.

(51) Int. Cl.
    *F03G 7/06* (2006.01)
    *G02B 23/24* (2006.01)
    *A61B 1/00* (2006.01)

(52) U.S. Cl.
    CPC .......... *F03G 7/065* (2013.01); *A61B 1/00* (2013.01); *F03G 7/06* (2013.01); *G02B 23/24* (2013.01)

(58) Field of Classification Search
    CPC .................................................. F03G 7/065
    USPC .................................. 60/527–529; 310/307
    See application file for complete search history.

(56) References Cited

U.S. PATENT DOCUMENTS

| 2006/0038643 | A1* | 2/2006 | Xu ..................... F03G 7/065 335/78 |
| 2006/0286835 | A1 | 12/2006 | Cheng et al. |
| 2012/0174571 | A1* | 7/2012 | Villanueva ............ F03G 7/065 60/527 |
| 2013/0000100 | A1 | 1/2013 | Szewczyk |

(Continued)

FOREIGN PATENT DOCUMENTS

| JP | S59-10789 A | 1/1984 |
| JP | 3122673 B2 | 1/2001 |
| JP | 3142928 B2 | 3/2001 |

(Continued)

OTHER PUBLICATIONS

International Search Report dated Jan. 31, 2017 issued in PCT/JP2016/082632.

(Continued)

*Primary Examiner* — Mark A Laurenzi
*Assistant Examiner* — Mickey H France
(74) *Attorney, Agent, or Firm* — Scully, Scott, Murphy & Presser, P.C.

(57) ABSTRACT

A variable stiffness actuator includes a shape-memory member capable of transitioning in phase between a first phase and a second phase. The shape-memory member takes a low-stiffness state when in the first phase, and takes a high-stiffness state. The variable stiffness actuator also includes an inducing member configured to cause the shape-memory member to transition in phase between the first phase and the second phase and a connecting member elastically connecting the shape-memory member and inducing member. All of the shape-memory member, the inducing member, and the connecting member are conductive, and the shape-memory member, the inducing member, and the connecting member are electrically connected to each other.

13 Claims, 8 Drawing Sheets

(56) References Cited

U.S. PATENT DOCUMENTS

2014/0255534 A1* 9/2014 Allen ................. F03G 7/005
                                                                425/542

FOREIGN PATENT DOCUMENTS

| JP | 2005-059188 A | 3/2005 |
|---|---|---|
| JP | 2013-521960 A | 6/2013 |
| WO | WO 2010/038564 a1 | 4/2010 |
| WO | WO 2016/121060 A1 | 8/2016 |

OTHER PUBLICATIONS

English Abstract of JP H05-168586 A dated Jul. 2, 1993.
English translation of International Preliminary Report on Patentability dated May 16, 2019, together with the Written Opinion received in related International Application No. PCT/JP2016/082632.

* cited by examiner

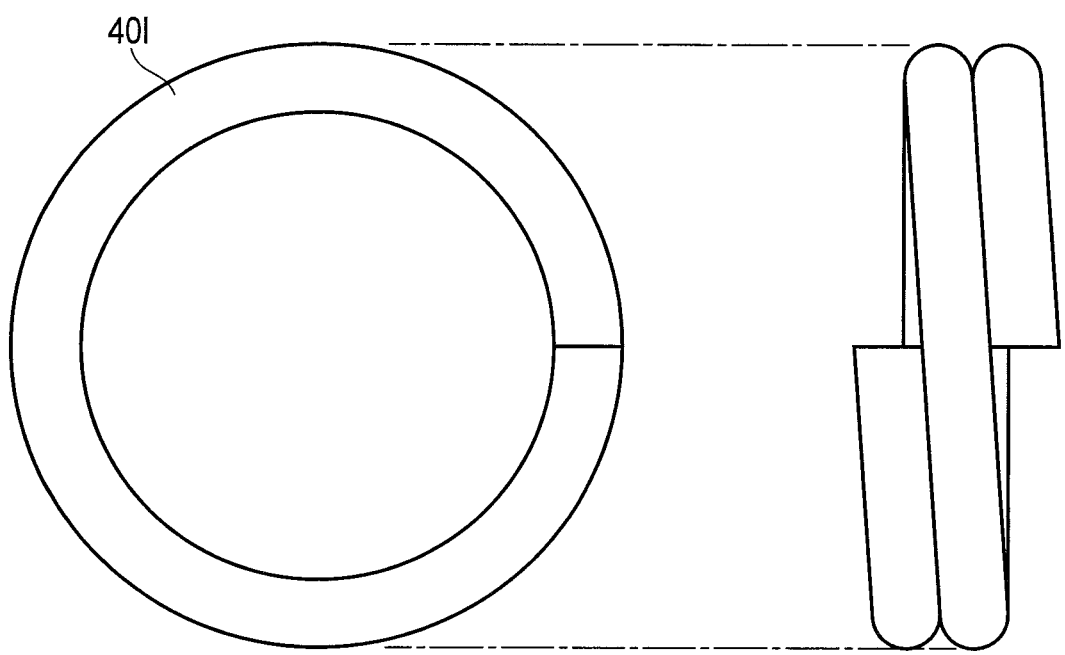
F I G. 12

VARIABLE STIFFNESS ACTUATOR

CROSS-REFERENCE TO RELATED APPLICATIONS

This application is a Continuation Application of PCT Application No. PCT/JP2016/082632, filed Nov. 2, 2016, the entire contents of which are incorporated herein by reference.

BACKGROUND OF THE INVENTION

Field of the Invention

The present invention relates to a variable stiffness actuator that is to be installed in a flexible member and is capable of changing the stiffness of the flexible member.

Description of the Related Art

Japanese Patent No. 3122673 discloses an endoscope capable of changing the stiffness of a flexible section of an insertion section. In this endoscope, both ends of a flexible member (such as a coil pipe) are fixed at predetermined positions in the endoscope, and a flexibility adjustment member (such as a flexibility adjustment wire inserted through a coil pipe) is fixed to the flexible member through a separator. The flexible member and the flexibility adjustment member extend to a control section of the endoscope along the flexible section and extend almost over the entire flexible section. The flexible member is compressed and stiffened by pulling the flexibility adjustment member, thereby varying the stiffness of the flexible section.

Japanese Patent No. 3142928 discloses a variable stiffness apparatus for a flexible tube using a shape-memory alloy. The variable stiffness apparatus includes a coil to be provided in a flexible tube, an electrical insulating tube provided inside the coil, a shape-memory alloyed wire arranged in the electrical insulating tube so as to extend in its axial direction, and an energization heating means for energizing the shape-memory alloyed wire.

The shape-memory alloyed wire has properties of elongating at a low temperature and contracting at a high temperature. The shape-memory alloyed wire extends out through fixed portions at both ends of the coil, and caulking members are fixed to the both ends. The shape-memory alloyed wire is arranged so that it loosens at a low temperature and it tightens up at a high temperature with the caulking members engaged with the fixed portions.

The shape-memory alloyed wire contracts to stiffen the coil at a high temperature at which it becomes energized by the energization heating means. On the other hand, the shape-memory alloyed wire elongates to soften the coil at a low temperature at which it does not is energized.

BRIEF SUMMARY OF THE INVENTION

A variable stiffness actuator includes a shape-memory member capable of transitioning in phase between a first phase and a second phase. The shape-memory member takes a low-stiffness state when in the first phase, and takes a high-stiffness state in which the shape-memory member has higher stiffness than in the low-stiffness state. The variable stiffness actuator also includes an inducing member configured to cause the shape-memory member to transition in phase between the first phase and the second phase and a connecting member elastically connecting the shape-memory member and the inducing member. All of the shape-memory member, the inducing member, and the connecting member are conductive, and the shape-memory member, the inducing member, and the connecting member are electrically connected to each other.

Advantages of the invention will be set forth in the description that follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 12 shows another connecting member applicable in place of the connecting member shown in FIG. 2.

DETAILED DESCRIPTION OF THE INVENTION

First Embodiment

Figure 1:
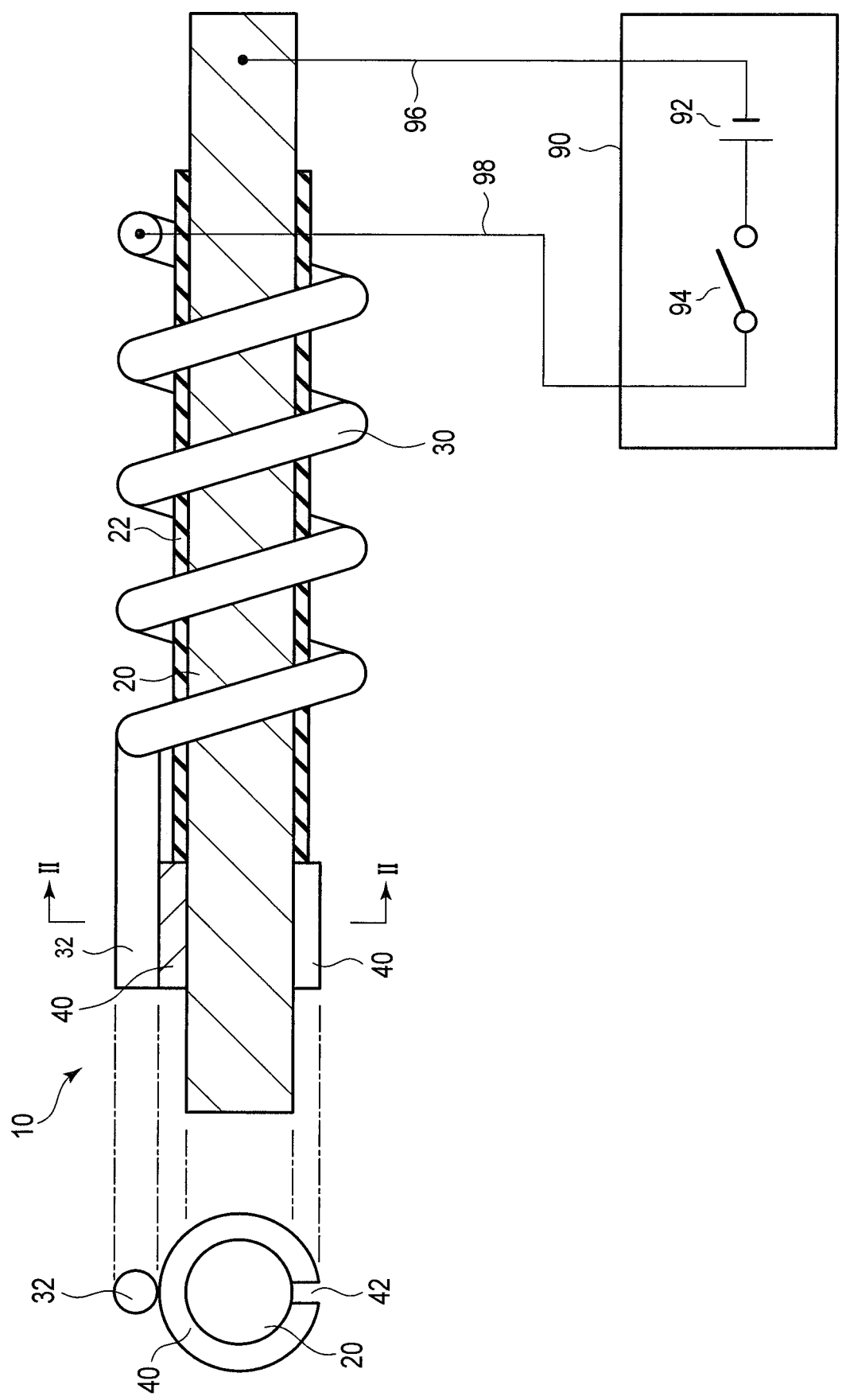
FIG. 1 shows a variable stiffness actuator according to a first embodiment.

FIG. 1 shows a variable stiffness actuator apparatus according to a first embodiment. As shown in FIG. 1, the variable stiffness actuator apparatus includes a variable stiffness actuator 10 capable of taking different stiffness states, and a controller 90 configured to control the stiffness states of the variable stiffness actuator 10.

The variable stiffness actuator 10 is to be installed in a flexible member, and has a function to provide different levels of stiffness to the flexible member by being capable of taking different stiffness states. The variable stiffness actuator 10 is to be installed in the flexible member so that a shape-memory member 20 has at least one free end.

The variable stiffness actuator 10 includes the shape-memory member 20 capable of transitioning in phase between a first phase and a second phase, an inducing member 30 configured to cause the shape-memory member 20 to transition in phase between the first phase and the second phase, and a connecting member 40 elastically connecting the shape-memory member 20 and the inducing member 30.

All of the shape-memory member 20, the inducing member 30, and the connecting member 40 are conductive. Accordingly, the shape-memory member 20, the inducing member 30, and the connecting member 40 are electrically connected to each other. Specifically, the shape-memory member 20 is electrically connected to the inducing member 30 through the connecting member 40.

The inducing member 30 is formed of a conductive material. The inducing member 30 has an end 32 fixed to the connecting member 40, for example, so that the inducing member 30 is electrically connected to the connecting member 40. Fixing between the inducing member 30 and the connecting member 40 may be performed by soldering, welding, conductive adhesive, brazing, etc. Such fixing manners are suitable for a variable stiffness actuator 10 that is small.

The connecting member 40 grasps the shape-memory member 20, thereby being electrically connected to the shape-memory member 20. This matter will be described later.

When the shape-memory member 20 is in the first phase, the shape-memory member 20 takes a low-stiffness state, namely, exhibits a low elastic modulus, and thus provides relatively low stiffness to the flexible member. When the shape-memory member 20 is in a second phase, the shape-memory member 20 takes a high-stiffness state in which the shape-memory member 20 is stiffer than in the low-stiffness state, namely, exhibits a high elastic modulus, and thus provides relatively high stiffness to the flexible member. The shape-memory member 20 tends to be easily deformed by an external force in the low-stiffness state, and tends to return to a memorized shape memorized in advance against the external force in the high-stiffness state. The memorized shape may be, but not limited to, a linear shape, for example.

Herein, the external force means a force that can deform the shape-memory member 20, and the gravity is considered to be part of the external force.

The inducing member 30 has the capability of generating heat. The shape-memory member 20 has a property of transitioning in phase from the first phase to the second phase by being heated by the heat generation of the inducing member 30.

The shape-memory member 20 may be formed of a shape-memory alloy, for example. The shape-memory alloy may be an alloy including, but not limited to, NiTi, for example.

The shape-memory alloy forming the shape-memory member 20 may be a shape-memory alloy that transitions in phase between a martensitic phase and an austenitic phase, for example. In the martensitic phase, the shape-memory alloy is plastically deformed relatively easily by an external force. In other words, the shape-memory alloy exhibits a low elastic modulus in the martensitic phase. In the austenitic phase, in contrast, the shape-memory alloy is not easily deformed by an external force. Even if the shape-memory alloy is deformed by a greater external force, the shape-memory alloy exhibits superelasticity and returns to a memorized shape when the greater external force is lost. In other words, the shape-memory alloy exhibits a high elastic modulus in the austenitic phase.

The inducing member 30 is formed of a conductive material, and has the property of generating heat in response to supply of a current. The inducing member 30 may be constituted by a heating wire, namely, a conductive member with large electrical resistance, for example.

The shape-memory member 20 has a slim exterior shape. The inducing member 30 is formed by a wire-like member, and is arranged around the outside of the shape-memory member 20. The inducing member 30 spirally extends around the shape-memory member 20 along the longitudinal axis of the shape-memory member 20 with an appropriate clearance from the shape-memory member 20. This configuration enables efficient conduction of heat generated by the inducing member 30 to the shape-memory member 20.

The shape-memory member 20 is formed of a conductive material. For example, an insulating film 22 is provided around the shape-memory member 20. The insulating film 22 serves to avoid a short circuit between the shape-memory member 20 and the inducing member 30.

Figure 2:
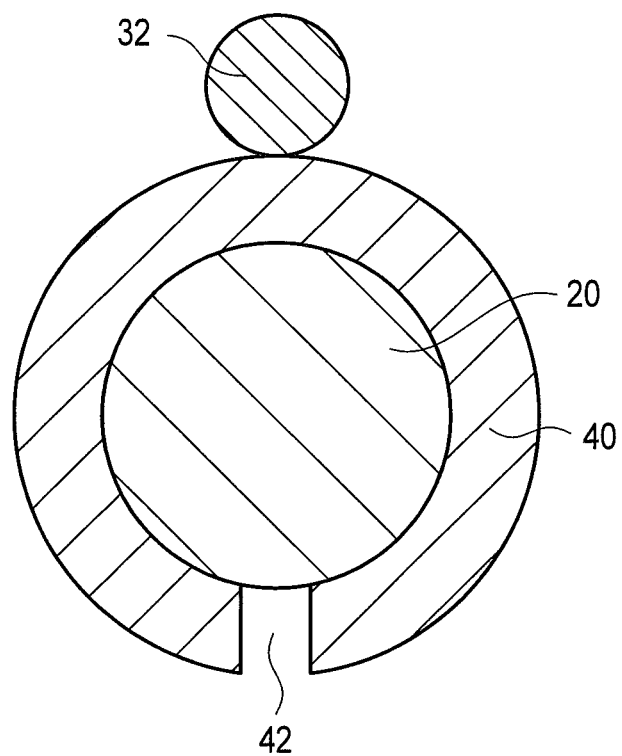
FIG. 2 schematically shows a cross-sectional structure of the variable stiffness actuator shown in FIG. 1, taken along line II-II.

FIG. 2 shows a cross-sectional structure of the variable stiffness actuator 10 shown in FIG. 1, taken along line II-II. As shown in FIG. 2, the shape-memory member 20 has a circular cross-section. The connecting member 40 has a C-shaped cross-section.

As understood from FIGS. 1 and 2, the shape-memory member 20 is formed into a circular column. The connecting member 40 is constituted by a circular cylinder that has a slit 42 along the longitudinal axis. Accordingly, the connecting member 40 has two ends along the circumference. Specifically, the connecting member 40 has two ends that are separate from each other along the circumference.

The connecting member 40 is arranged to surround the shape-memory member 20 and to be in contact with the shape-memory member 20. The connecting member 40 is configured to be deformed flexibly and elastically. An inner diameter of the connecting member 40 is set slightly smaller than an outer diameter of the shape-memory member 20. In other words, the connecting member 40 is arranged around the shape-memory member 20 with the connecting member 40 being opened slightly more than the original state. As a result, the connecting member 40 grasps the shape-memory member 20 by a restoring force to elastically deform inwards.

The end 32 of the inducing member 30 is fixed to a portion of the connecting member 40 opposite to the slit 42. The position to which the end 32 of the inducing member 30 is fixed is not limited to the portion of the connecting member 40 opposite to the slit 42, and may be other suitable portions of the connecting member 40. However, the portion of the connecting member 40 opposite to the slit 42 is least deformed in response to deformation of the shape-memory member 20; thus, the portion of the connecting member 40 opposite to the slit 42 is the most preferable position for fixing the end 32 of the inducing member 30 to.

The shape of the shape-memory member 20 is not limited to a circular column, and may be an elliptic column or a polygonal column. If the shape-memory member 20 is formed into an elliptic column, it is preferable that the inner diameter of the connecting member 40 is set to be slightly smaller than a diameter of the ellipse of the cross-section of the shape-memory member 20 along the long axis of the ellipse. If the shape-memory member 20 is formed into a polygonal column, it is preferable that the inner diameter of the connecting member 40 is set to be slightly smaller than the largest diameter of the polygon of the cross-section of the shape-memory member 20. The connecting member 40 may be formed into an elliptic cylinder or a polygonal cylinder, corresponding to a shape of the shape-memory member 20. In this case, it is preferable that the inner outline of the connecting member 40 is set to be slightly smaller than the outer outline of the shape-memory member 20, in a cross-section perpendicular to the longitudinal axis.

As shown in FIG. 1, the controller 90 includes a power source 92 and a switch 94. The power source 92 and the switch 94 are electrically connected to each other. The power source 92 is electrically connected to the shape-memory member 20 through a wire 96. The switch 94 is electrically connected to the inducing member 30 through a wire 98. The controller 90 supplies a current to the inducing member 30 in response to ON, namely, a closing operation, of the switch 94, and stops supplying a current to the inducing member 30 in response to OFF, namely, an opening operation, of the switch 94. The inducing member 30 generates heat in response to supply of a current.

The above-described variable stiffness actuator 10 is installed in a flexible member, without restraining both ends of the shape-memory member 20. For example, the variable stiffness actuator 10 is arranged in a limited space of the flexible member with a small gap so that an end or both ends of the shape-memory member 20 are a free end or free ends.

Herein, the limited space means a space of a size just capable of containing the variable stiffness actuator 10 therein. Accordingly, even if deformation of either one of the variable stiffness actuator 10 or the flexible member is slight, it may come into contact with the other and give an external force to the other.

For example, the flexible member may be a tube having an inner diameter slightly larger than the outer diameter of the variable stiffness actuator 10, and the variable stiffness actuator 10 may be arranged inside the tube. The configuration of the flexible member is not limited to this, and the flexible member only has to have a space slightly larger than the variable stiffness actuator 10.

When the shape-memory member 20 is in the first phase, the variable stiffness actuator 10 provides relatively low stiffness to the flexible member, and is easily deformed by an external force exerted on the flexible member, namely, a force capable of deforming the shape-memory member 20.

When the shape-memory member 20 is in the second phase, the variable stiffness actuator 10 provides relatively high stiffness to the flexible member, and tends to return to its memorized shape against an external force exerted on the flexible member, namely, a force capable of deforming the shape-memory member 20.

For example, the stiffness of the flexible member is switched by switching the phase of the shape-memory member 20 between the first phase and the second phase by the controller 90.

In addition to the switching of the stiffness, the variable stiffness actuator 10 also functions as a bidirectional actuator that switches the shape of the flexible member, when an external force is being exerted on the flexible member. The variable stiffness actuator 10 also functions as a unidirectional actuator that causes the flexible member to return to the original shape, when no external force is exerted on the flexible member and the flexible member is deformed in the first phase before the phase of the shape-memory member 20 is switched to the second phase.

Figure 3:
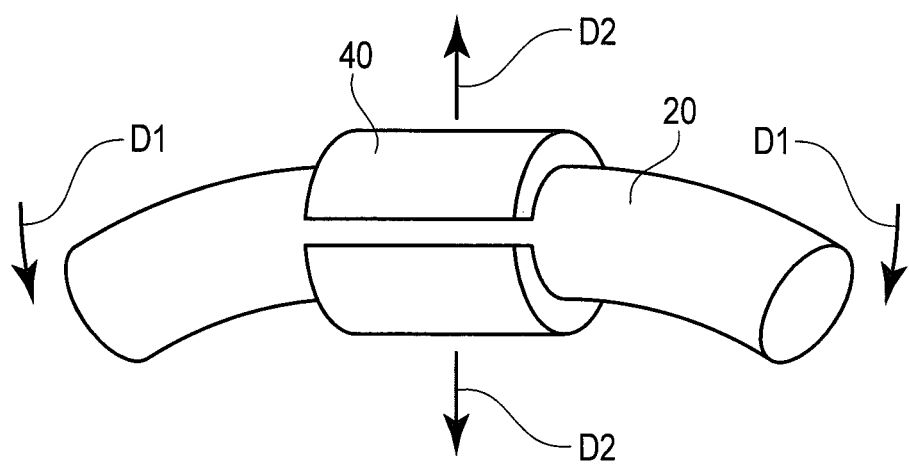
FIG. 3 schematically shows bending deformation of a shape-memory member and deformation of a connecting member in response to the bending deformation of the shape-memory member.

FIG. 3 schematically shows bending deformation of the shape-memory member 20 and deformation of the connecting member 40 in response to the bending deformation of the shape-memory member 20. The shape-memory member 20 can be easily deformed to bend in accordance with an external force when the shape-memory member 20 is in the first phase. If the shape-memory member 20 is deformed to bend, the shape-memory member 20 is deformed in an arc direction (indicated by an arrow D1) from the end of the shape-memory member 20 in a straight state toward the end of the shape-memory member 20 in a bent state. If the shape-memory member 20 is deformed to bend near the connecting member 40, the connecting member 40 is deformed outwards in a radial direction of the connecting member 40 (indicated by an arrow D2) in response to the bending deformation of the shape-memory member 20. In other words, the connecting member 40 converts the direction of the bending deformation of the shape-memory member 20 to a direction perpendicular to the longitudinal axis of the shape-memory member 20, namely, the radial direction of the connecting member 40.

As a comparative example, assume a variable stiffness actuator in which the end 32 of the inducing member 30 extends parallel to the shape-memory member 20 and is directly fixed to the shape-memory member 20 without interposing the connecting member 40 therebetween. In such a variable stiffness actuator, if the shape-memory member 20 is deformed to bend, the portion where the end 32 of the inducing member 30 is fixed to the shape-memory member 20 directly receives the stress due to the bending deformation of the shape-memory member 20. This may cause damage or breakage of the electric connection between the inducing member 30 and the shape-memory member 20.

In contrast, in the variable stiffness actuator 10 of the present embodiment, the end 32 of the inducing member 30 extends parallel to the shape-memory member 20, and is fixed to the connecting member 40 that grasps the shape-memory member 20. Accordingly, the portion where the end 32 of the inducing member 30 is fixed to the connecting member 40 receives little stress due to the bending deformation of the shape-memory member 20, and mostly only moves in a direction so that the connecting member 40 is opened further. In other words, the stress that is applied to the portion where the end 32 of the inducing member 30 is fixed to the connecting member 40 due to the bending deformation of the shape-memory member 20 is greatly reduced. This greatly reduces the possibility of damaging or breaking the electric connection between the inducing member 30 and the shape-memory member 20 due to the bending deformation of the shape-memory member 20.

The shorter the connecting member 40 is, the less the portion where the end 32 of the inducing member 30 is fixed to the connecting member 40 is affected by the deformation of the shape-memory member 20. Thus, the connecting member 40 is preferably as short as possible in the range where a sufficient force for grasping the shape-memory member 20 is obtained.

[Various Alternatives to Connecting Member 40]

Various alternatives, which are applicable in place of the connecting member 40 shown in FIG. 2, will be described with reference to FIGS. 4 to 12. As a matter of course, all of the connecting members in the alternatives shown in FIGS. 4 to 12 are conductive. FIGS. 4 to 11 schematically show cross-sectional structures corresponding to the cross-section shown in FIG. 1, taken along line II-II.

[Connecting Member According to First Alternative]

Figure 4:
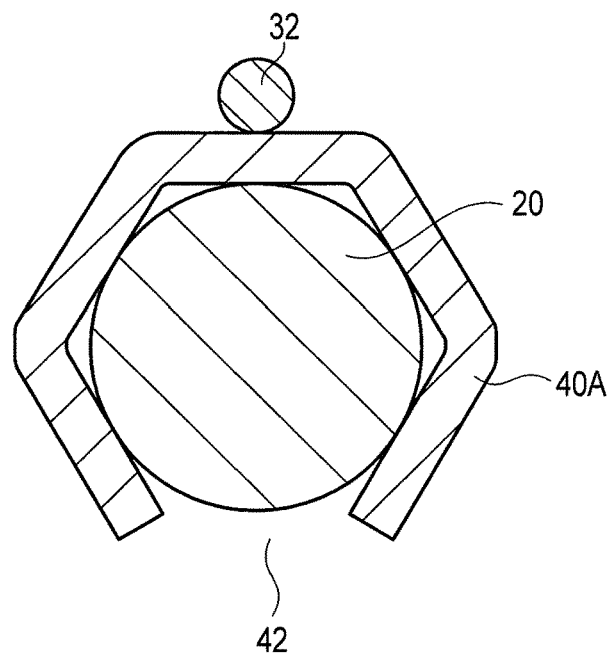
FIG. 4 shows another connecting member applicable in place of the connecting member shown in FIG. 2.

FIG. 4 shows another connecting member 40A applicable in place of the connecting member 40 shown in FIG. 2. The connecting member 40A is constituted by a polygonal cylinder that has a slit 42 along the longitudinal axis. The connecting member 40A is arranged to surround the shape-memory member 20 and to be in contact with the shape-memory member 20. The connecting member 40A is configured to be deformed flexibly and elastically. A diameter of the inscribed circle of the inner outline of the connecting member 40A is set slightly smaller than the outer diameter of the shape-memory member 20. In other words, the connecting member 40A is arranged around the shape-memory member 20 with the connecting member 40A being opened slightly more than the original state. As a result, the connecting member 40A grasps the shape-memory member 20 by a restoring force to elastically deform inwards.

The end 32 of the inducing member 30 is fixed to a portion of the connecting member 40A opposite to the slit 42. The position to which the end 32 of the inducing member 30 is fixed is not limited to the portion of the connecting member 40A opposite to the slit 42, and may be other suitable portions of the connecting member 40A.

Similarly to the connecting member 40 in a circular-cylindrical shape, also in the connecting member 40A in a polygonal-cylindrical shape, the portion where the end 32 of the inducing member 30 is fixed to the connecting member 40A receives little stress due to the bending deformation of the shape-memory member 20, and mostly only moves in a direction so that the connecting member 40A is opened further. In other words, the stress that is applied to the portion where the end 32 of the inducing member 30 is fixed to the connecting member 40A due to the bending deformation of the shape-memory member 20 is greatly reduced. This greatly reduces the possibility of damaging or breaking the electric connection between the inducing member 30 and the shape-memory member 20 due to the bending deformation of the shape-memory member 20.

The contact points of the connecting member 40A in a polygonal-cylindrical shape can be designed more discretionarily than the connecting member 40 in a circular-cylindrical shape. In other words, the number of contact points between the connecting member 40A and the shape-memory member 20 can be determined discretionarily. In the circular-cylindrical connecting member 40 as shown in FIG. 2, the number of the contact points between the connecting member 40 and the shape-memory member 20 is not actually known. In the drawing, the connecting member 40 appears to be closely attached to the shape-memory member 20 over the entire surface; however, such state seems unrealistic. In other words, the number of the contact points between the connecting member 40 and the shape-memory member 20 is considered to vary. Such variation in the number of the contact points may cause variation in a resistance value and a grasping force. In contrast, in the connecting member 40A in a polygonal-cylindrical shape, the number of the contact points can be determined precisely; accordingly, variation in the number of the contact points can be reduced, and thus variation in a resistance value and variation in a grasping force can be reduced.

[Connecting Member According to Second Alternative]

Figure 5:
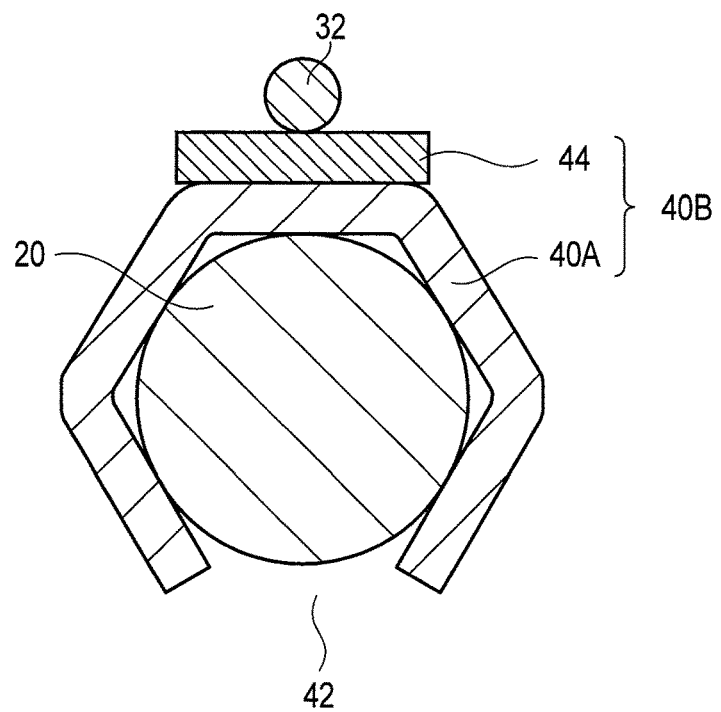
FIG. 5 shows another connecting member applicable in place of the connecting member shown in FIG. 2.

FIG. 5 shows another connecting member 40B applicable in place of the connecting member 40 shown in FIG. 2. The connecting member 40B is constituted by the connecting member 40A shown in FIG. 4 and a reinforcement member 44 fixed to the connecting member 40A. The reinforcement member 44 is formed of a conductive material. The reinforcement member 44 may be formed of a rectangular plate-like member. The reinforcement member 44 is fixed to a portion of the connecting member 40A opposite to the slit 42. The reinforcement member 44 serves to increase stiffness of the portion of the connecting member 40A opposite to the slit 42. The reinforcement member 44 constitutes a high-stiffness portion that increases stiffness of a part of the connecting member 40A. In other words, the connecting member 40B has a high-stiffness portion that has higher stiffness than the other portion. The end 32 of the inducing member 30 is fixed to the reinforcement member 44.

Since the end 32 of the inducing member 30 is fixed to the high-stiffness portion of the connecting member 40B, namely the reinforcement member 44, the stress that is applied to the portion where the end 32 of the inducing member 30 is fixed to the connecting member 40B due to the bending deformation of the shape-memory member 20 is further reduced. As a result, the possibility of damaging or breaking the electric connection between the inducing member 30 and the shape-memory member 20 is further reduced.

[Connecting Member According to Third Alternative]

Figure 6:
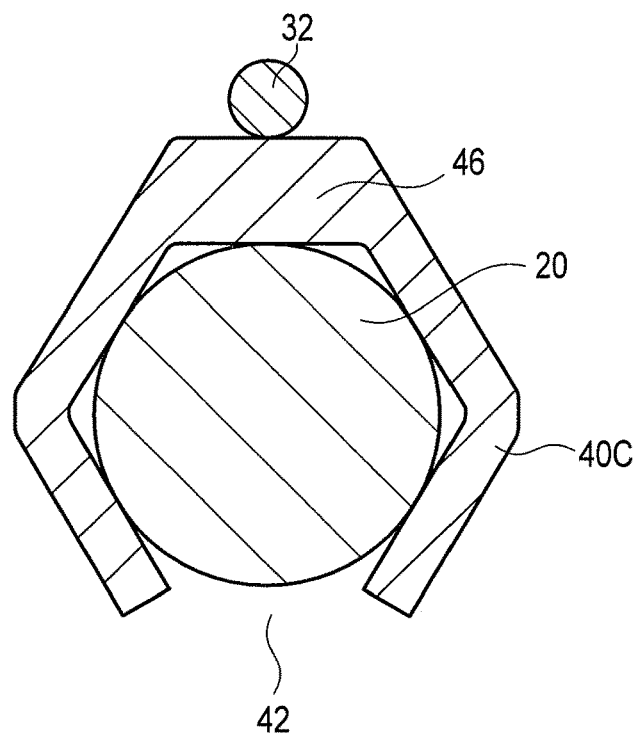
FIG. 6 shows another connecting member applicable in place of the connecting member shown in FIG. 2.

FIG. 6 shows another connecting member 40C applicable in place of the connecting member 40 shown in FIG. 2. Similarly to the connecting member 40A shown in FIG. 4, the connecting member 40C is constituted by a polygonal cylinder that has a slit 42 along the longitudinal axis. In the connecting member 40C, a portion of the connecting member 40C opposite to the slit 42 is formed to be thick. In other words, the portion of the connecting member 40C opposite to the slit 42 has higher stiffness than the other portion. Specifically, the connecting member 40C has a high-stiffness portion 46 that has higher stiffness than the other portion. The end 32 of the inducing member 30 is fixed to the high-stiffness portion 46 of the connecting member 40C, namely, a portion of the connecting member 40C opposite to the slit 42.

Since the end 32 of the inducing member 30 is fixed to the high-stiffness portion of the connecting member 40C, the stress that is applied to the portion where the end 32 of the inducing member 30 is fixed to the connecting member 40C due to the bending deformation of the shape-memory member 20 is further reduced. As a result, the possibility of damaging or breaking the electric connection between the inducing member 30 and the shape-memory member 20 is further reduced.

[Connecting Member According to Fourth Alternative]

Figure 7:
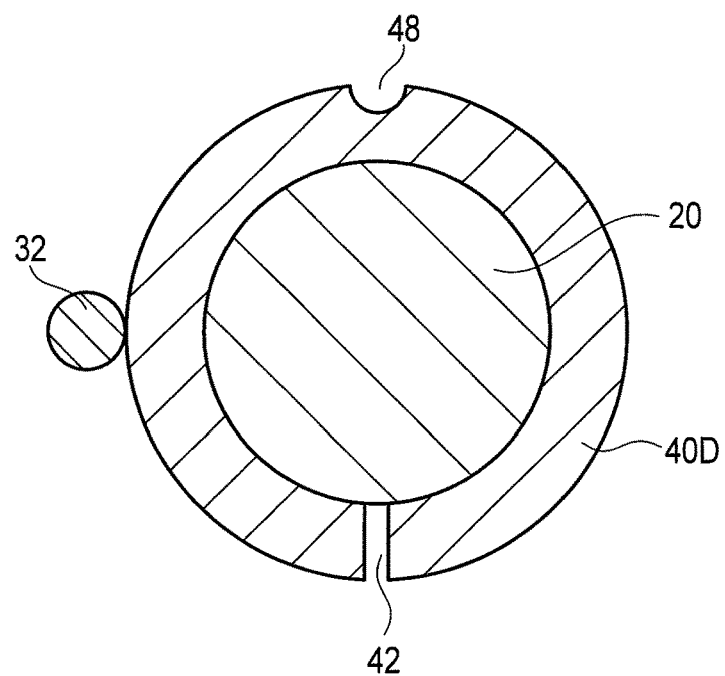
FIG. 7 shows another connecting member applicable in place of the connecting member shown in FIG. 2.

FIG. 7 shows another connecting member 40D applicable in place of the connecting member 40 shown in FIG. 2. Similarly to the connecting member 40 shown in FIG. 2, the connecting member 40D is constituted by a circular cylinder that has a slit 42 along the longitudinal axis. The connecting member 40D has a portion with a reduced board thickness. For example, a groove 48 is formed on the connecting member 40D. The groove 48 is formed on a portion of the connecting member 40D opposite to the slit 42, for example. The groove 48 extends along the axis of the connecting member 40D in a linear manner, for example. The portion of the connecting member 40D near the groove 48 has lower stiffness than the other portion. In other words, the connecting member 40D has a low-stiffness portion that has lower stiffness than the other portion. The end 32 of the inducing member 30 is fixed to a portion of the connecting member 40D away from the low-stiffness portion, for example, in the middle between the slit 42 and the groove 48.

In the connecting member 40D, in response to the bending deformation of the shape-memory member 20, the low-stiffness portion, namely, the portion near the groove 48, is deformed more largely than the other portion. Since the end 32 of the inducing member 30 is fixed to the portion of the connecting member 40D away from the low-stiffness portion, the stress that is applied to the portion where the end 32 of the inducing member 30 is fixed to the connecting member 40D due to the bending deformation of the shape-memory member 20 is favorably reduced. As a result, the possibility of damaging or breaking the electric connection between the inducing member 30 and the shape-memory member 20 is favorably reduced.

[Connecting Member According to Fifth Alternative]

Figure 8:
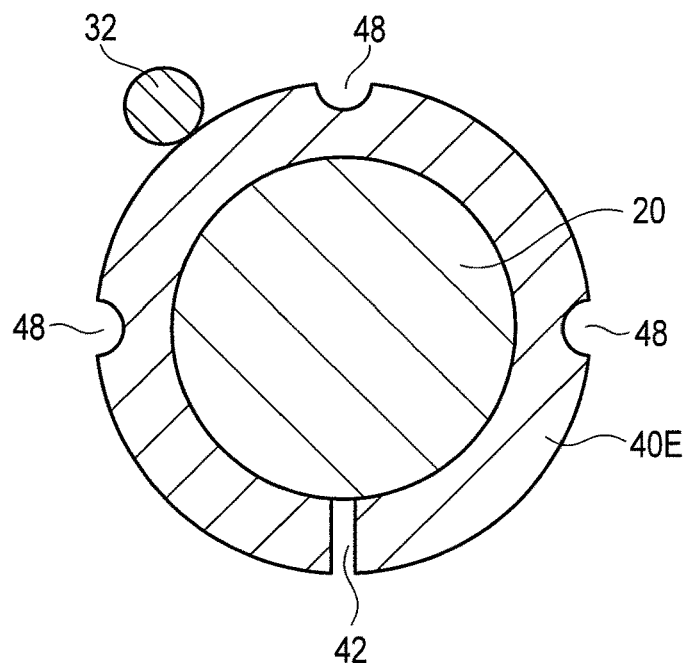
FIG. 8 shows another connecting member applicable in place of the connecting member shown in FIG. 2.

FIG. 8 shows another connecting member 40E applicable in place of the connecting member 40 shown in FIG. 2. Similarly to the connecting member 40D shown in FIG. 7, the connecting member 40E is constituted by a circular cylinder that has a slit 42 along the longitudinal axis. The connecting member 40E has portions with a reduced board thickness. For example, grooves 48 are formed on the connecting member 40E. For example, three grooves 48 are formed around the axis of the connecting member 40E with an interval of the same angle, such as 90°, symmetrically relative to the slit 42. The grooves 48 extend along the axis of the connecting member 40E in a linear manner, for example. The portions of the connecting member 40E near the groove 48 have lower stiffness than the other portion. In other words, the connecting member 40E has low-stiffness portions that have lower stiffness than the other portion. The end 32 of the inducing member 30 is fixed to a portion of the connecting member 40E away from the low-stiffness portions, for example, in the middle between two grooves 48. The end 32 of the inducing member 30 may be fixed to a portion in the middle between the slit 42 and a groove 48, for example.

In the connecting member 40E, in response to the bending deformation of the shape-memory member 20, the low-stiffness portions, namely, the portions near the grooves 48, are deformed more largely than the other portion. Since the connecting member 40E has the low-stiffness portions, a deformed amount of each low-stiffness portion of the connecting member 40E is smaller than a deformed amount of the low-stiffness portion of the connecting member 40D having only one low-stiffness portion, and the stress on each low-stiffness portion of the connecting member 40E is smaller than the stress on the low-stiffness portion of the connecting member 40D.

Since the end 32 of the inducing member 30 is fixed to the portion of the connecting member 40E away from the low-stiffness portions, the stress that is applied to the portion where the end 32 of the inducing member 30 is fixed to the connecting member 40E due to the bending deformation of the shape-memory member 20 is favorably reduced. As a result, the possibility of damaging or breaking the electric connection between the inducing member 30 and the shape-memory member 20 is favorably reduced. [Connecting Member According to Sixth Alternative]

Figure 9:
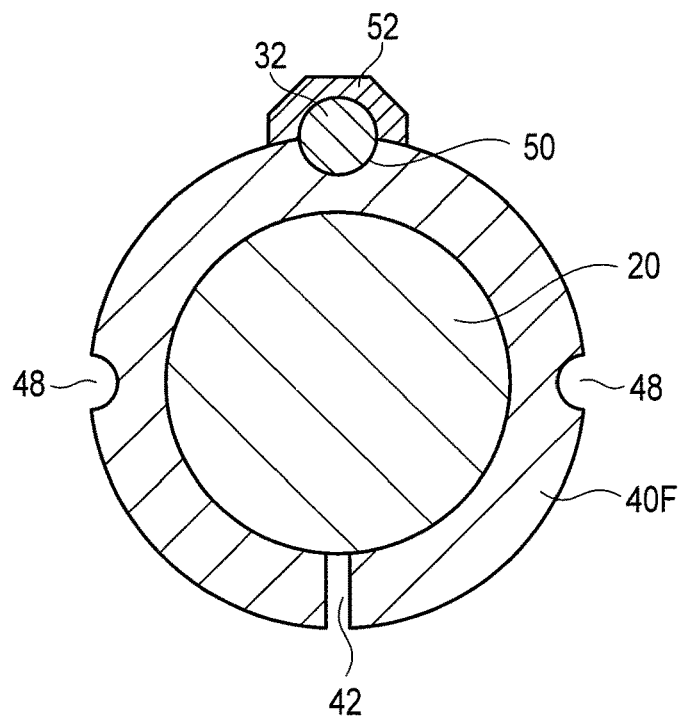
FIG. 9 shows another connecting member applicable in place of the connecting member shown in FIG. 2.

FIG. 9 shows another connecting member 40F applicable in place of the connecting member 40 shown in FIG. 2. Similarly to the connecting member 40E shown in FIG. 8, the connecting member 40F is constituted by a circular cylinder having a slit 42 along the longitudinal axis, and has portions with a reduced board thickness such as two grooves 48. On the connecting member 40F, a groove 50 to receive the end 32 of the inducing member 30 is formed. The end 32 of the inducing member 30 is arranged along the groove 50. A fixing member 52 is provided to cover the end 32, and fixes the end 32 to the connecting member 40F. In other words, the end 32 of the inducing member 30 and the connecting member 40F are fixed to each other by the fixing member. For example, the groove 50 is formed on a portion of the connecting member 40F opposite to the slit 42, and the two grooves 48 are each formed in the middle between the slit 42 and the groove 50; however, the configuration is not limited thereto.

The portions of the connecting member 40F near the grooves 48 have lower stiffness than the other portion. In other words, the connecting member 40F has low-stiffness portions that have lower stiffness than the other portion.

The fixing member 52 may be formed by thickly applying solder, conductive adhesive, and wax. The fixing member 52 has moderately high stiffness, and serves to increase stiffness of the portion of the connecting member 40F where the fixing member 52 is provided. In other words, the fixing member 52 constitutes a high-stiffness portion that increases stiffness of a part of the connecting member 40F. In other words, the connecting member 40F has a high-stiffness portion that has higher stiffness than the other portion. From another perspective, the fixing member 52 is used in place of the high-stiffness portion.

Since the connecting member 40F has the low-stiffness portions similarly to the connecting member 40E, the stress on each low-stiffness portion of the connecting member 40F is smaller than the stress on the low-stiffness portion of the connecting member 40D having the only one low-stiffness portion.

Since the end 32 of the inducing member 30 is fixed to the high-stiffness portion constituted by the fixing member 52, the stress that is applied to the portion where the end 32 of the inducing member 30 is fixed to the connecting member 40F due to the bending deformation of the shape-memory member 20 is favorably reduced. As a result, the possibility of damaging or breaking the electric connection between the inducing member 30 and the shape-memory member 20 is favorably reduced.

[Connecting Member According to Seventh Alternative]

Figure 10:
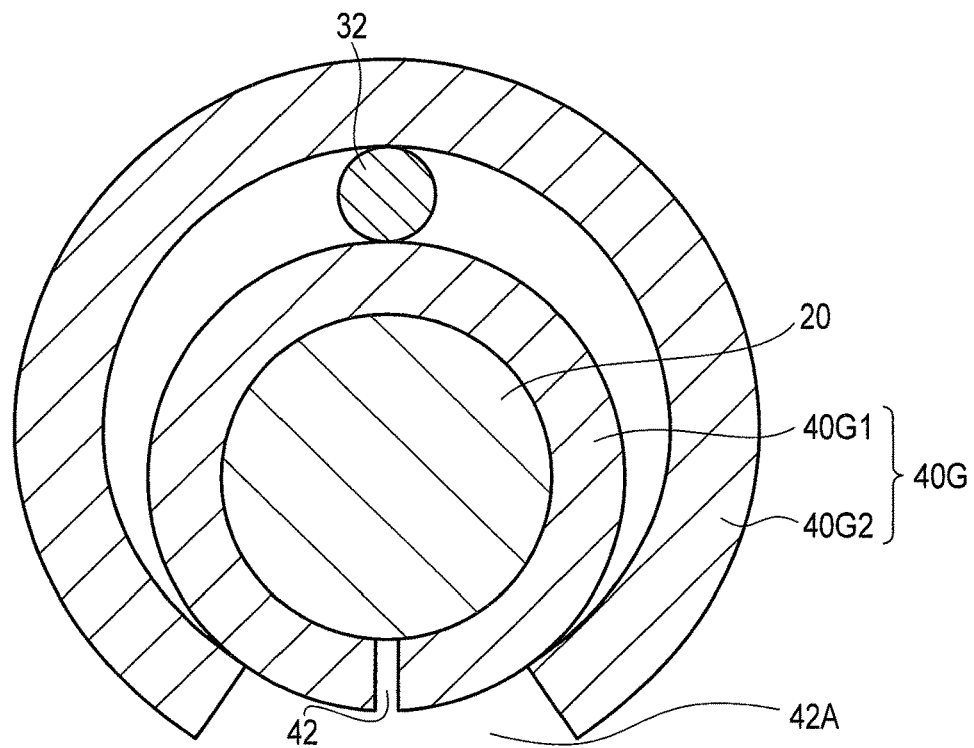
FIG. 10 shows another connecting member applicable in place of the connecting member shown in FIG. 2.

FIG. 10 shows another connecting member 40G applicable in place of the connecting member 40 shown in FIG. 2. The connecting member 40G is constituted by a first connecting member 40G1 and a second connecting member 40G2. The first connecting member 40G1 is configured in a similar manner to the connecting member 40 shown in FIG. 2. However, the end 32 of the inducing member 30 is not fixed to the first connecting member 40G1. The second connecting member 40G2 is constituted by a circular cylinder that has a slit 42A along the longitudinal axis. The second connecting member 40G2 is arranged to surround the first connecting member 40G1 and to be in contact with the first connecting member 40G1, so that the end 32 of the inducing member 30 is pinched between the first connecting member 40G1 and the second connecting member 40G2.

The second connecting member 40G2 is configured to be deformed flexibly and elastically. The second connecting member 40G2 is arranged around the first connecting member 40G1 with the second connecting member 40G2 being opened slightly more than the original state. As a result, the second connecting member 40G2 pushes the end 32 of the inducing member 30 against the first connecting member 40G1 by a restoring force to elastically deform inwards. In other words, the connecting member 40G holds the end 32 of the inducing member 30 by an elastic force of the second connecting member 40G2. As a result, stable electric connection is provided between the end 32 of the inducing member 30 and the first connecting member 40G1.

The end 32 of the inducing member 30 is not fixed to the first connecting member 40G1, and is pinched and held between the first connecting member 40G1 and the second connecting member 40G2. Accordingly, the electric connection between the end 32 of the inducing member 30 and the first connecting member 40G1 is scarcely affected by the bending deformation of the shape-memory member 20. As a result, the possibility of damaging or breaking the electric connection between the inducing member 30 and the shape-memory member 20 is favorably reduced.

[Connecting Member According to Eighth Alternative]

Figure 11:
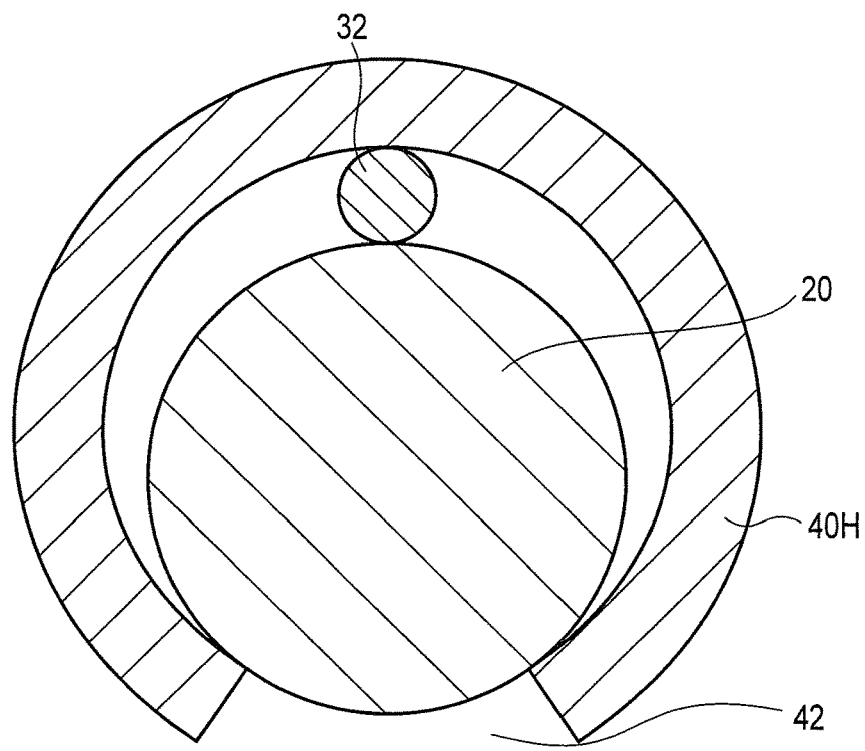
FIG. 11 shows another connecting member applicable in place of the connecting member shown in FIG. 2.

FIG. 11 shows another connecting member 40H applicable in place of the connecting member 40 shown in FIG. 2. The connecting member 40H is constituted by a circular cylinder that has a slit 42 along the longitudinal axis. The connecting member 40H is arranged to surround the shape-memory member 20 and to be in contact with the shape-memory member 20, so that the end 32 of the inducing member 30 is pinched between the connecting member 40H and the shape-memory member 20.

The connecting member 40H is configured to be deformed flexibly and elastically. The connecting member 40H is arranged around the shape-memory member 20 with the connecting member 40H being opened slightly more than the original state. As a result, the connecting member 40H pushes the end 32 of the inducing member 30 against the shape-memory member 20 by a restoring force to elastically deform inwards. In other words, the connecting member 40H holds the end 32 of the inducing member 30 by an elastic force of the connecting member 40H in cooperation with the shape-memory member 20. As a result, stable electric connection is provided between the end 32 of the inducing member 30 and the shape-memory member 20.

Since the end 32 of the inducing member 30 is pinched and held between the connecting member 40H and the shape-memory member 20, the electric connection between the end 32 of the inducing member 30 and the shape-memory member 20 is scarcely affected by the bending deformation of the shape-memory member 20. As a result, the possibility of damaging or breaking the electric connection between the inducing member 30 and the shape-memory member 20 is favorably reduced.

[Connecting Member According to Ninth Alternative]

FIG. 12 shows another connecting member 40I applicable in place of the connecting member 40 shown in FIG. 2. The connecting member 40I is formed into a coil-spring shape. In other words, the connecting member 40I is configured to spirally wind into circles that are more than one and adjacent to each other. The connecting member 40I is configured to be deformed flexibly and elastically. An inner diameter of the connecting member 40I is set slightly smaller than the outer diameter of the shape-memory member 20. When the connecting member 40I is attached to the shape-memory member 20, the connecting member 40I is arranged around the shape-memory member 20 with the connecting member 40I being opened slightly more than the original state. As a result, the connecting member 40I grasps the shape-memory member 20 by a restoring force to elastically deform inwards.

The end 32 of the inducing member 30 is fixed to the outer periphery of the connecting member 40I, for example, on a portion away from both ends.

In response to the bending deformation of the shape-memory member 20, the connecting member 40I is deformed to increase its diameter. Accordingly, the stress that is applied to the portion where the end 32 of the inducing member 30 is fixed to the connecting member 40I due to the bending deformation of the shape-memory member 20 is greatly reduced. This leads to great reduction of the possibility of damaging or breaking the electric connection between the inducing member 30 and the shape-memory member 20 due to the bending deformation of the shape-memory member 20.

Second Embodiment

Figure 13:
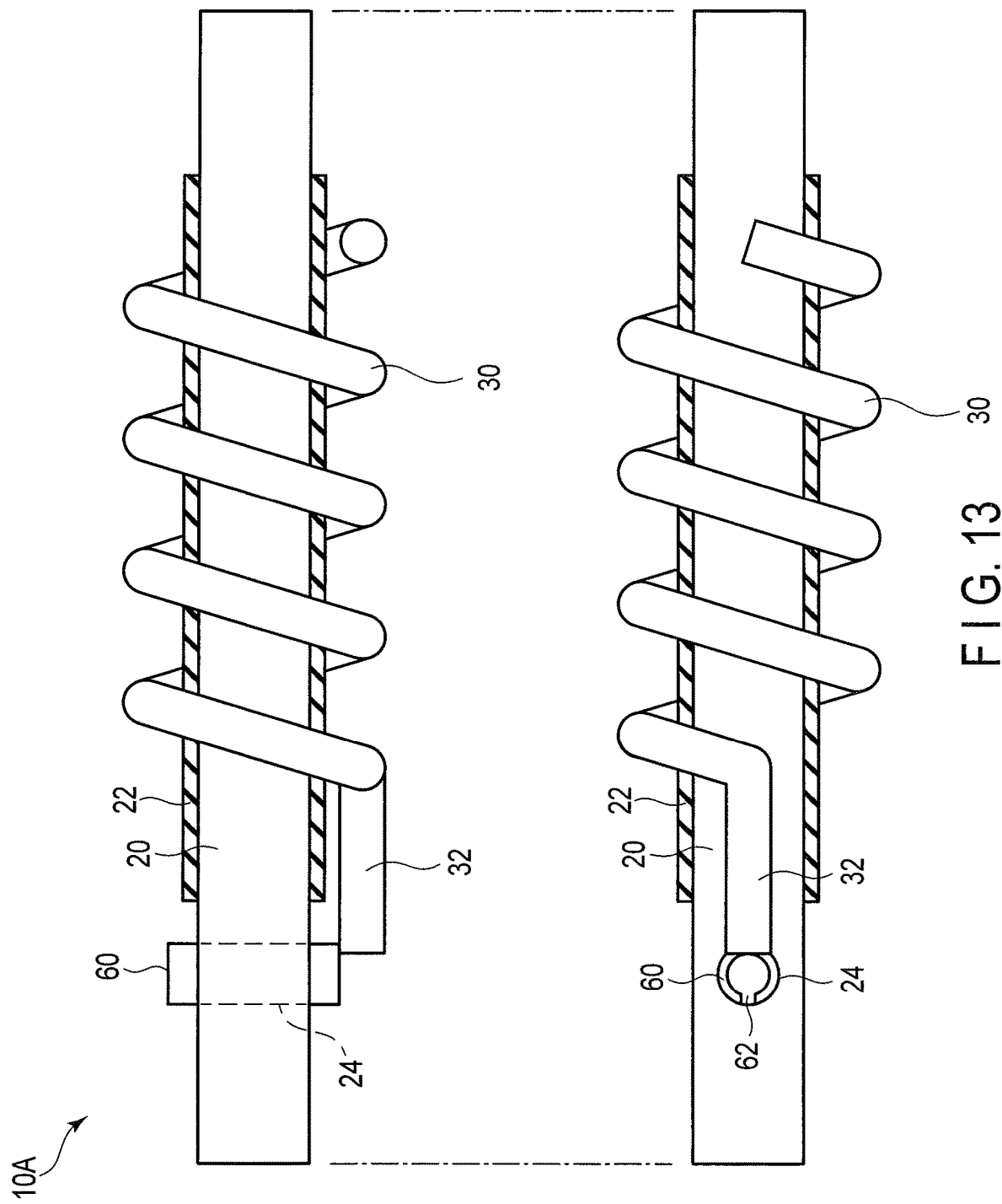
FIG. 13 shows a variable stiffness actuator according to a second embodiment.

FIG. 13 shows a variable stiffness actuator 10A according to a second embodiment. As shown in FIG. 13, the variable stiffness actuator 10A includes a shape-memory member 20, an inducing member 30, a connecting member 60 elastically connecting the shape-memory member 20 and the inducing member 30. The configurations of the shape-memory member 20 and the inducing member 30 are the same as those described in the first embodiment.

All of the shape-memory member 20, the inducing member 30, and the connecting member 60 are conductive. Thus, the shape-memory member 20, the inducing member 30, and the connecting member 60 are electrically connected to each other. Specifically, the shape-memory member 20 is electrically connected to the inducing member 30 through the connecting member 60.

The shape-memory member 20 is provided with a circular through hole 24. The through hole 24 extends across the axis of the shape-memory member 20; for example, extends perpendicularly to the axis of the shape-memory member 20. The connecting member 60 is constituted by a circular cylinder that has a slit 62 along the longitudinal axis. The diameter of the through hole 24 is smaller than the outer diameter of the connecting member 60. The connecting member 60 is pressed into the through hole 24. As a result, the connecting member 60 is held by the shape-memory member 20.

The end 32 of the inducing member 30 is fixed to a part of an end of the connecting member 60, so that the inducing member 30 is electrically connected to the connecting member 60. For example, the end 32 of the inducing member 30 is fixed to a part of the end of the connecting member 60 that is located opposite to the slit 62. Fixing between the inducing member 30 and the connecting member 60 may be performed by soldering, welding, conductive adhesive, brazing, etc. Such fixing manners are suitable for a variable stiffness actuator 10A that is small.

The shape-memory member 20 can be easily deformed to bend in accordance with an external force when the shape-memory member 20 is in the first phase. If the shape-memory member 20 is deformed to bend near the connecting member 60, the connecting member 60 is deformed inwards in a radial direction of the connecting member 60 in response to the bending deformation of the shape-memory member 20. Thus, the portion where the end 32 of the inducing member 30 is fixed to the connecting member 60 receives little stress due to the bending deformation of the shape-memory member 20. Furthermore, the stress that is applied to the portion where the end 32 of the inducing member 30 is fixed to the connecting member 60 due to the bending deformation of the shape-memory member 20 is greatly reduced. This leads to great reduction of the possibility of damaging or breaking the electric connection between the inducing member 30 and the shape-memory member 20 due to the bending deformation of the shape-memory member 20.

The through hole 24 formed in the shape-memory member 20 is not limited to a circular through hole, and may be a through hole in other shapes; for example, an elliptic through hole and a polygonal through hole. The connecting member 60 is not limited to a circular cylinder having a slit, and may be a cylinder in other shapes having a slit; for example, an elliptic cylinder or a polygonal cylinder having a slit. The connecting member 60 may have a high-stiffness portion, a low-stiffness portion, or a fixing portion. The above modifications would be easily analogized from some of the alternatives of the connecting member 40 shown in FIGS. 4 to 9.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A variable stiffness actuator that is to be installed in a flexible member and is capable of providing different levels of stiffness to the flexible member, the variable stiffness actuator comprising:
   a shape-memory member having a columnar shape, the shape-memory member being capable of transitioning in phase between a first phase and a second phase, the shape-memory member having a first stiffness when in the first phase, and having a second stiffness when in the second phase, the second stiffness being higher than the first stiffness;
   an inducing member arranged along an axial direction of the shape-memory member so as to circumferentially surround the shape-memory member, the inducing member being configured to generate heat by being supplied with a current to cause the shape-memory member to transition in phase between the first phase and the second phase by heating the shape-memory member; and
   a connecting member elastically connecting the shape-memory member to an end of the inducing member,
   each of the shape-memory member, the inducing member, and the connecting member being conductive, the shape-memory member, the inducing member, and the connecting member being electrically connected to each other.

2. The variable stiffness actuator according to claim 1, wherein the shape-memory member is electrically connected to the inducing member through the connecting member.

3. The variable stiffness actuator according to claim 1, wherein the connecting member has a tubular shape having a slit, the connecting member being radially enlarged against a restoring force to elastically deform inwards, so as to fix the connecting member to the shape-memory member by the restoring force.

4. The variable stiffness actuator according to claim 1, wherein the inducing member is fixed to the connecting member.

5. The variable stiffness actuator according to claim 3, wherein the connecting member is deformed outwards in response to bending deformation of the shape-memory member.

6. The variable stiffness actuator according to claim 1, wherein the connecting member has a high-stiffness portion that has higher stiffness than other portions of the connecting member.

7. The variable stiffness actuator according to claim 1, wherein the connecting member has a low-stiffness portion that has lower stiffness than other portions of the connecting member.

8. The variable stiffness actuator according to claim 4, wherein the connecting member and the inducing member are fixed to each other by a fixing member.

9. The variable stiffness actuator according to claim 8, wherein the fixing member increases stiffness of a portion of the connecting member where the fixing member is provided as compared to other portions of the connecting member.

10. The variable stiffness actuator according to claim 1, wherein the connecting member has a columnar shape having a slit along an axis and is arranged around the shape-memory member with being spread out against a restoring force, so that the inducing member is pinched between the connecting member and the shape-memory member, and the connecting member holds the inducing member by the restoring force pressing the inducing member against the shape-memory member.

11. The variable stiffness actuator according to claim 1, wherein the shape-memory member is provided with a hole having a smaller diameter than an outer diameter of the connecting member, and the connecting member is pressed into the hole.

12. The variable-stiffness actuator according to claim 1, wherein the connecting member connects the shape-memory member and only the end of the inducing member.

13. The variable-stiffness actuator according to claim 1, wherein the inducing member is helically wound around an outer circumferential periphery of the shape-memory member.

* * * * *